(12) United States Patent
Mullens et al.

(10) Patent No.: US 9,464,342 B2
(45) Date of Patent: Oct. 11, 2016

(54) TITANIUM, TITANIUM ALLOY AND NITI FOAMS WITH HIGH DUCTILITY

(71) Applicant: Vlaamse Instelling Voor Technologisch Onderzoek (VITO), Mol (BE)

(72) Inventors: Steven Mullens, Zichem (BE); Ivo Thijs, Mol (BE); Jozef Cooymans, Mol (BE); Jan Luyten, Molenstede (BE)

(73) Assignee: VLAAMSE INSTELLING VOOR TECHNOLOGISCH ONDERZOEK (VITO), Mol (BE)

(*) Notice: Subject to any disclaimer, the term of this patent is extended or adjusted under 35 U.S.C. 154(b) by 0 days.

(21) Appl. No.: 14/667,403

(22) Filed: Mar. 24, 2015

(65) Prior Publication Data

US 2015/0240331 A1    Aug. 27, 2015

Related U.S. Application Data

(63) Continuation of application No. 11/916,877, filed as application No. PCT/BE2006/000066 on Jun. 7, 2006, now Pat. No. 8,992,828.

(30) Foreign Application Priority Data

Jun. 7, 2005 (EP) .................... 05447131

(51) Int. Cl.
*C22C 1/04* (2006.01)
*C22C 1/08* (2006.01)
(Continued)

(52) U.S. Cl.
CPC . *C22C 1/08* (2013.01); *A61F 2/28* (2013.01); *B22F 3/1017* (2013.01);
(Continued)

(58) Field of Classification Search
None
See application file for complete search history.

(56) References Cited

U.S. PATENT DOCUMENTS 5,846,664 A    12/1998    Third et al.
6,228,299 B1    5/2001    Janney et al.
(Continued)

FOREIGN PATENT DOCUMENTS

EP    0765704 A2    4/1997
EP    1329439 A1    7/2003
(Continued)

OTHER PUBLICATIONS

Murray et al., "Microstructure Evolution During Solid-State Foaming of Titanium," 2311-2316 Composites Sci. and Tech. 63 (2003), 6 pages.
(Continued)

*Primary Examiner* — Yoshitoshi Takeuchi
(74) *Attorney, Agent, or Firm* — Merchant & Gould P.C.

(57) ABSTRACT

A method for manufacturing a high ductility Ti-, Ti-alloy or NiTi-foam, meaning a compression strain higher than 10%, includes: preparing a powder suspension of a Ti-, NiTi- or Ti-alloy powder, bringing the said powder suspension into a desired form by gelcasting to form a green artifact. The method also includes a calcination step wherein the green artifact is calcined, and sintering the artifact. The calcination step includes a slow heating step wherein said green artifact is heated at a rate lower or equal to 20° C./hour to a temperature between 400° C. and 600° C. and the Ti-, NiTi- or Ti-alloy powder has a particle size less than 100 μm. A high ductility Ti-, Ti-alloy or NiTi foam, with a compression higher than 10%, with a theoretical density less than 30%, pore size (cell size) between 50 to 1000 μm can be obtained with such a method.

6 Claims, 3 Drawing Sheets

(51) Int. Cl.
*B22F 3/10* (2006.01)
*B22F 3/11* (2006.01)
*A61F 2/28* (2006.01)
*C22C 14/00* (2006.01)
*C22C 19/03* (2006.01)

(52) U.S. Cl.
CPC ............ *B22F 3/1121* (2013.01); *C22C 14/00* (2013.01); *C22C 19/03* (2013.01); *B22F 2998/00* (2013.01); *Y10T 428/12479* (2015.01)

(56) References Cited

U.S. PATENT DOCUMENTS

2005/0048193 A1* 3/2005 Li .......................... A61L 27/04
427/2.24
2005/0207928 A1* 9/2005 Shimizu ................ B22F 3/1125
419/2
2007/0048164 A1 3/2007 Demetriou et al.

FOREIGN PATENT DOCUMENTS

| EP | 1731247 A1 | 12/2006 |
| JP | 2001-271101 | 10/2001 |
| JP | 2002-285203 | 10/2002 |

OTHER PUBLICATIONS

Janney, Mark A., "Gelcasting Superalloy Powders," Metals and Ceramics Division, Oak Ridge National Laboratory, Oak Ridge, TN (1996), 8 pages.

* cited by examiner

TITANIUM, TITANIUM ALLOY AND NITI FOAMS WITH HIGH DUCTILITY

This application is a continuation of U.S. patent application Ser. No. 11/916,877, filed Jul. 1, 2008, which is a National Stage Application of PCT/BE2006/000066, filed Jun. 7, 2006, which claims benefit of Serial No. 05447131.3, filed Jun. 7, 2005 in Europe and which application(s) are incorporated herein by reference. To the extent appropriate, a claim of priority is made to each of the above disclosed applications.

FIELD OF THE INVENTION

The present invention is related to high ductility titanium, titanium alloy or NiTi foams, in particular for use in biomedical or composite structures. The invention relates also to the use of such foams as bone replacement or healing aid.

STATE OF THE ART

Titanium, titanium alloys and NiTi are commonly used for their high strength/weight ratio, their high resistance to corrosion and relatively low elasticity modulus, and their biocompatibility. The mechanical properties of Ti-foams are very close to bone properties and therefore, it seems the select material for bone replacement or healing aid. However, this application requires high ductility foams. Ductility is more commonly defined as the ability of a material to deform easily upon the application of a tensile force, or as the ability of a material to withstand plastic deformation without rupture, breaking or fracturing. Ductility may also be thought of in terms of bend ability and crushability. Ductile materials show large deformation before fracture. The lack of ductility is often termed brittleness.

Titanium is very reactive with a lot of compounds if heated above 300° C. Due to interstitial incorporation of elements like N, O, C or H in the Ti, a brittle foam is obtained, lacking strength and ductility (or insufficient fatigue properties) to serve as a high-quality bone replacement.

Some manufacturing procedures of these metallic foams require large relative quantities of organic materials (which are used as additives in the suspension preparation or which serve as template for the porous structure like e.g. in the polyurethane replica technique). As such, the residual contamination of elements like N, O, C or H will be much higher, resulting in an embrittlement of the metallic foam. Typical ductility values for Ti foams manufactured by the polyurethane replica technique is about 3% in strain.

On the other hand, low contamination with N, O, C and thus high ductility can be seen as a consequence of the use of the gelcasting procedure as the shaping method.

AIMS OF THE INVENTION

The present invention aims to provide a method for the production of high-ductility Ti, Ti-alloy and NiTi foams.

The present invention also aims at providing a high-ductility, highly porous (>70% total porosity) Ti, Ti-alloy and NiTi foams. Preferably, a minimum plastic deformation of 10% without rupture, breaking or fracturing should be achieved.

SUMMARY OF THE INVENTION

The present invention concerns a method for manufacturing a high ductility Ti-, Ti-alloy- or NiTi-foam, meaning that the metallic structure can be deformed more than 10% in compression without rupture, comprising the steps of
  Preparing a powder suspension of a Ti-, NiTi- or Ti-alloy powder,
  Bring said powder suspension into a desired form by gelcasting to form a green artefact,
  A calcination step wherein said green artefact is calcined, and
  Sintering said artefact,
characterised in that said calcination step comprises a slow heating step wherein said green artefact is heated at a rate lower or equal to 20° C./hour to a temperature between 400° C. and 600° C. and that the Ti-, NiTi- or Ti-alloy powder has a particle size less than 100 μm.

Preferably, said calcinations step is performed under an inert atmosphere or at a pressure less than $10^{-3}$ mbar.

The method according to the present invention can further comprise a presintering step comprising heating the artefact until a temperature of between 900 and 1000° C. is reached.

It can also comprise a sintering step comprising slow heating of the artefact to a temperature between 1200° C. and 1500° C., and keeping said artefact at said temperature for a predetermined period of time.

In a preferred embodiment, the powder comprises less than 0.03 weight % C, less than 0.8 weight % O, less than 0.5 weight % N, less than 0.1 weight % Fe and less than 0.1 weight % Si.

The powder suspension can be brought into the desired form using gelcasting.

Another aspect of the present invention concerns the high ductility of the highly porous Ti-, Ti-alloy or NiTi-foams with a theoretical density less than High ductility means that these Ti-foams can be deformed in compression for more then 10%. A certain plasticity is a minimum requirement for load bearing implants.

SHORT DESCRIPTION OF THE DRAWINGS

DETAILED DESCRIPTION OF THE INVENTION

A more detailed description of the present invention is presented by means of examples and figures. The general process according to the present invention is given in FIG. 1.

Figure 1:
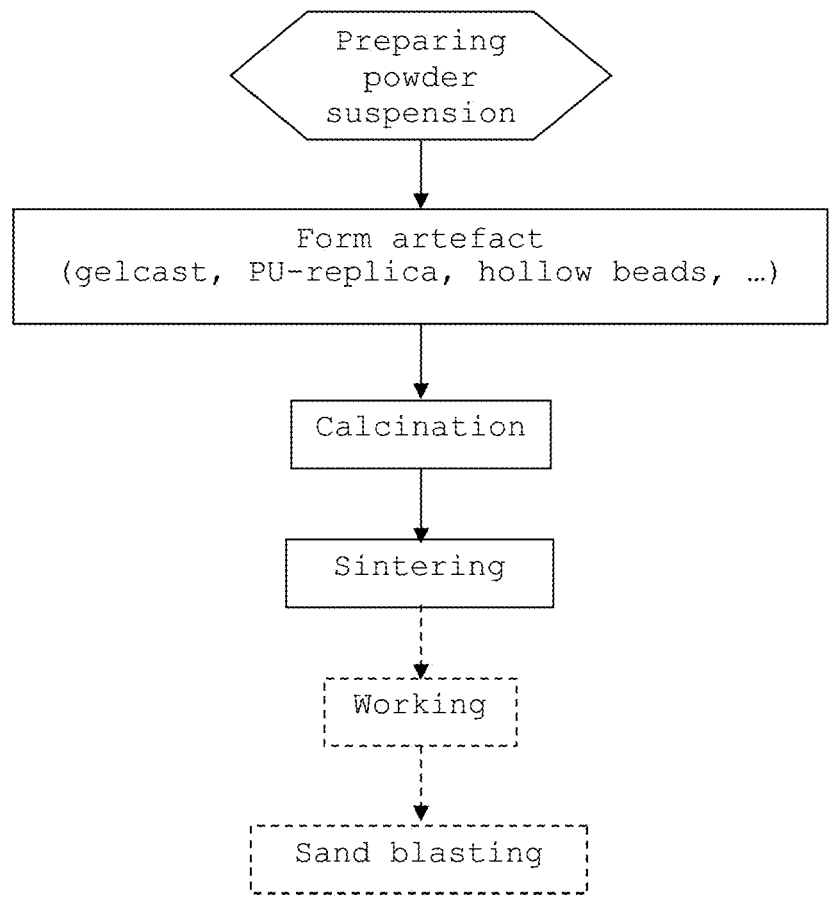
FIG. 1 represents a flowchart of the general method according to the present invention.

The powder suspension is prepared by mixing water and Ti-powder (or powder of a Ti-alloy such as Ti6Al4V, or NiTi-powder), with a powder volume between 20 and 50 vol %) with additives such as dispersing agents and gelling aids. The skilled person is well acquainted with these additives and can easily prepare a suitable powder suspension according to this first step of the process, suitable for the gelcasting forming process. Also, the viscosity of the suspension can be easily adapted to the desired range suitable for gelcasting. Examples of gelling aids and other additives, which can be used for obtaining a stable Ti-, Ti-alloy or NiTi-suspension according to the known methods as presented in the forming step of FIG. 1, are below:

Gelling aids:
  Gelatine
  Agarose
  Other hydrocolloids or biobinders (pectins, starch, xanthane, carragene, . . . )
Other Additives
  Cellulose-derived (e.g. hydroxypropyl methylcellulose)
  Alginate and its derivatives
  Dispersion agents (such as Targon™ 1128, DarvanC™, . . . )
  Foaming agents In order to obtain a suitable suspension for the process according to the present invention, the particle size of the metallic powder should be less than 100 µm, the particle shape should be spherical or irregular (depending on the milling method) and of high purity, with less than 0.03 weight % C, less than 0.8 weight % O, less than 0.5 weight % N, less than 0.1 weight % H, less than 0.1 weight % Fe and less than 0.1 weight % Si. The particle size of the Ti-powder has to be between 10 and 100 µm for the following reasons: —Ti-powder with particle size under 10 µm has a too high oxygen quantity ($TiO_2$ on their surface); On the other hand this kind of Ti-powders are too pyrophore for easy handling. Ti-powder, particle sizes above 100 µm, gives problems in the preparation of the slurry as sedimentation of the suspension occurs.

Gelcasting with hydrocolloids or biobinders as gelling agent produces a highly porous structure (70-90% of the theoretical density), an open pore network in which the pore dimensions ranges between 50 and 1000 µm (depending on the powder suspension and process parameters such as type and quantity of foaming agent, viscosity of the suspension, foaming procedure, . . . ) and a high interconnectivity.

The calcination step is preferably executed in two steps. In the first step, a slow heating (maximum 20° C. per hour) until a temperature of 400 to 600° C. is obtained (preferably less than 500° C.).

A too high calcination rate has to be prevented:
  it prevents cracking of the green product
  carbon residues have to be minimized because carbon take-up by the Ti-scaffold is directly related to his brittleness Advantageously, this is done under inert atmosphere such as argon or at low pressure (minimum of $10^{-3}$ mbar). During this first step, most of the organic material present will be burnt away.

The second step of the calcination step is a presintering step until a temperature of 900 to 1000° C. is reached. This results in a structure where the Ti powder particles already start to sinter together, allowing handling of the structure. Preferably, this step is performed under a vacuum of at least $10^{-4}$ mbar on a Mo plate or on a $Y_2O_3$— (coated) substrate.

Next, the obtained structure is sintered by placing it on Mo or a $Y_2O_3$— (coated) strips or rolls, allowing a further shrinking of the structure. Again, a high vacuum of more than $10^{-4}$ mbar is used. If necessary, the Ti foam can be co-sintered to a dense Ti structure.

Optionally, a working step can be used in case it is necessary to remove e.g. reaction zones situated at the contact points with the Mo support material or when other structure corrections (e.g. sawing) are desired.

Figure 2:
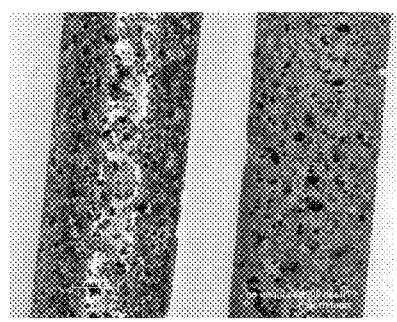
FIGS. 2a and 2b represent the effects of sandblasting on the surface of a Ti-foam which was manufactured according to the present invention. The artefact surface is shown before (FIG. 2a) and after (FIG. 2b) the sandblasting operation.

Also, a sandblasting operation can be useful to further remove the semi-closed pore windows at the surface of the artefact. The result of such a sandblasting operation can be seen in FIG. 2 b.

EXAMPLES

1. Ti Foam Structure Obtained by Gelcasting:

A suspension is prepared using 300 g Ti (Cerac; 99, 5% pure; −325 mesh), 201 g $H_2O$, 6.4 g Agar (3, 18% on $H_2O$), 6 g Tergitol TMN10 (2% on Ti), 3 g Triton (1% on Ti) and 0.36 g Ammonium Alginate (0, 18% on $H_2O$). It is mixed during 6 minutes at 70° C. to obtain a fluid foam. The foam is cast into a mould and cooled down until the structure is gelled. After demoulding, the structure is dried at atmospheric pressure and room temperature.

Figure 3:
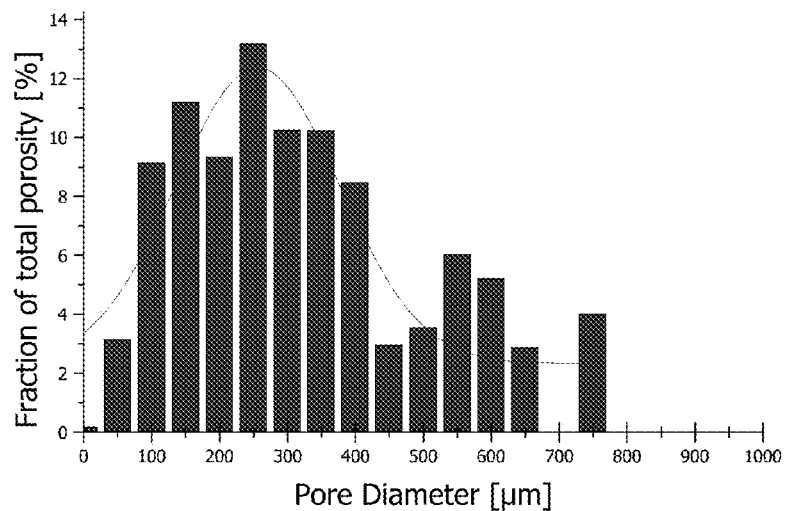
FIG. 3 shows a typical pore size distribution of a Ti foam structure obtained by gelcasting according to the present invention.
Figure 4:
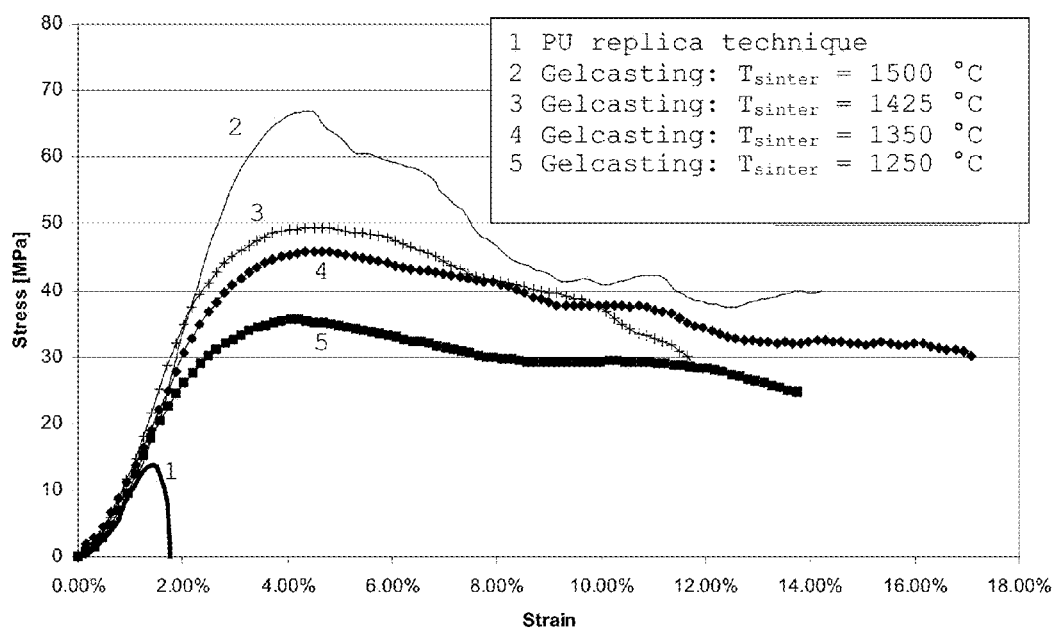
FIG. 4 shows the relation between stress and deformation for several sintering temperatures for a foam according to the present invention and compares it with these of a Ti foam manufactured by PU replica technique.

The structure is then calcined ($10^{-3}$ mbar, 20° C./h until 500° C., 2 hours isotherm, in the presence of Zr metal) and sintered ($10^{-4}$ mbar, 5° C./min to 1200-1500° C.; 2 h isotherm). An open-structured Ti foam with pore size between 50 and 1000 µm is obtained. A typical pore size distribution is shown in FIG. 3. The influence of the sinter temperature on the stress-strain curve of gelcasted Ti-foams is presented in FIG. 4. As a comparison, the stress-strain curves for ti-foams manufactured by the polyurethane technique is presented, showing the great difference in ductility between the 2 techniques. The tests were performed on Ti-foams, cutted in cylinders of diameter 16 mm and a height of 20 mm, compressed on a conventional Instron Machine, with a compression speed of 2 mm/min.

Properties of the obtainable structures include (depending on sintering temperature):

| E-modulus (GPa) | |
| --- | --- |
| 1500° C. | 2.5 |
| 1425° C. | 2.1 |
| 1350° C. | 1.8 |
| 1250° C. | 1.5 |
| Specific surface (m²/g) | |
| 1500° C. | 0.7 |
| 1250° C. | 1.3 |
| Porosity (% TD) | |
| 1500° C. | 70% |
| 1250° C. | 75% | as can be seen from the stress-strain curves, deformation higher than 10% is obtained.

2. TiAl64V Foams

A Ti-6Al-4V-suspension was prepared, similar to the composition in example 1, using a Ti-6Al-4V powder with a similar particle size distribution. After gelcasting and sintering, cylindric samples were cut and compressed (condition similar to example 1: sample dimensions: diameter 16 mm and height 20 mm; tests were performed on a Instron-equipment using a compression speed of 2 mm/min).

For a foam density of 17% of the theoretical density, the compression stress was 34 MPa and a strain of more the 24% could be obtained.

3. NiTi Foams

NiTi can also be used for producing foams. An example is a NiTi-foam created with the gelcasting technique.

Figure 5:
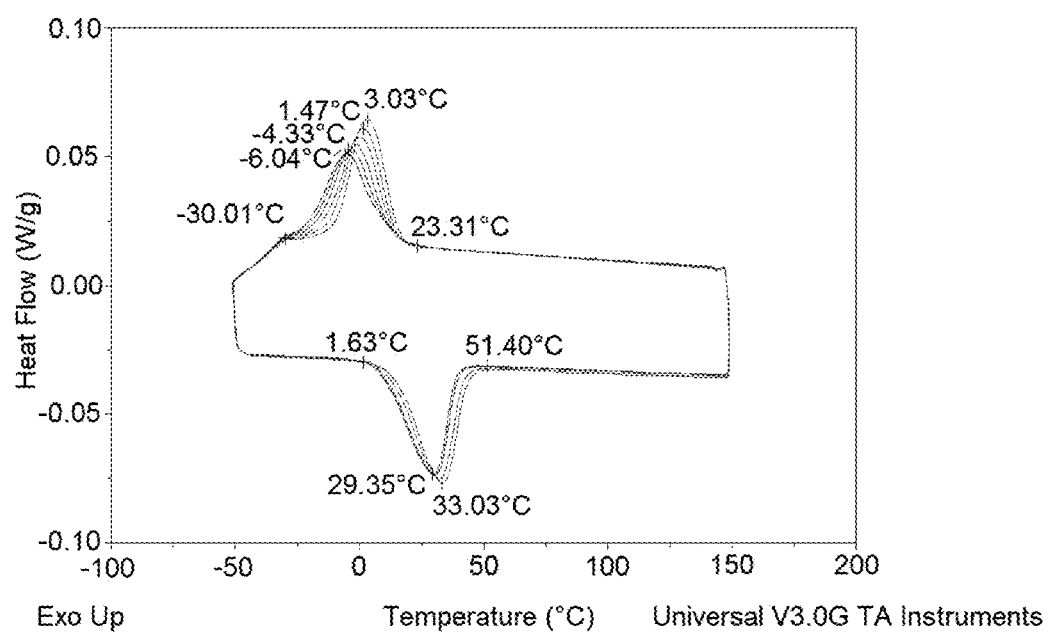
FIG. 5 shows the shape memory effect of a NiTi foam structure obtained according to the present invention.

Differential Scanning calorimetry (DSC, TA Instruments 2920) was used to measure the shape memory effect of such a foam. The transition temperature is clear from FIG. 5. These materials are very promising for biomedical applications as the transitions occur at body temperature.

The existence of this Shape Memory Effect (SME) and the sharp transition peak in the DSC-profile which could be demonstrated is an indirect proof of a low contamination of O, N, C. Such low contamination as specific property of the gelcasting process, will result in a high ductility, even further improved by the pseudo-elasticity of the alloy used.

The invention claimed is:

1. A titanium foam or titanium alloy foam with a density less than 30% of the theoretical density and a pore size between 50 and 1000 μm,
    which has a compressive strength of at least 34 MPa and
    which has a strain in compression for of more than 10% without rupture.

2. The foam of claim 1, having an E-modulus between 1.5 and 2.5 GPa.

3. The foam of claim 1, having a specific surface between 0.7 and 1.3 $m^2/g$.

4. The foam of claim 1, having a porosity higher than 70% and less than or equal to 90% of the theoretical density.

5. The foam of claim 1, wherein the strain in compression of more than 10% is a plastic deformation.

6. An implant comprising the foam of claim 1.

* * * * *